United States Patent
Von Bünau et al.

(10) Patent No.: US 9,144,375 B2
(45) Date of Patent: Sep. 29, 2015

(54) METHOD FOR DETERMINING THE POWER OF AN INTRAOCULAR LENS

(75) Inventors: Rudolf Murai Von Bünau, Jena (DE); Burkhart Wagner, Jena (DE); Scott A. Meyer, Livermore, CA (US); Xunchang Chen, Pleasanton, CA (US)

(73) Assignee: Carl Zeiss Meditec AG, Jena (DE)

( * ) Notice: Subject to any disclaimer, the term of this patent is extended or adjusted under 35 U.S.C. 154(b) by 637 days.

(21) Appl. No.: 12/630,656

(22) Filed: Dec. 3, 2009

(65) Prior Publication Data
US 2010/0134763 A1  Jun. 3, 2010

Related U.S. Application Data

(63) Continuation of application No. PCT/EP2008/004406, filed on Jun. 3, 2008.

(60) Provisional application No. 60/933,012, filed on Jun. 4, 2007.

(51) Int. Cl.
*A61B 3/00* (2006.01)
*A61F 2/16* (2006.01)

(52) U.S. Cl.
CPC .................. *A61B 3/0025* (2013.01); *A61F 2/16* (2013.01)

(58) Field of Classification Search
USPC .................. 351/245–247, 212, 211, 221, 200, 351/159.01, 159.06, 159.07, 159.74; 623/5.11, 6.11, 6.14, 6.22, 6.23, 6.34, 623/6.36, 6.24, 6.25, 6.26, 6.27, 5–907, 623/6.56; 600/452
See application file for complete search history.

(56) References Cited

U.S. PATENT DOCUMENTS

| | | | | |
|---|---|---|---|---|
| 4,710,193 A | * | 12/1987 | Volk | 623/6.23 |
| 5,282,852 A | * | 2/1994 | Capetan et al. | 623/6.11 |
| 6,004,314 A | * | 12/1999 | Wei et al. | 606/12 |
| 6,634,751 B2 | * | 10/2003 | Turner et al. | 351/212 |
| 8,087,782 B2 | * | 1/2012 | Norrby | 351/246 |

FOREIGN PATENT DOCUMENTS

| | | |
|---|---|---|
| WO | WO 03/022137 A2 | 3/2003 |
| WO | WO 2005/030044 A1 | 4/2005 |

OTHER PUBLICATIONS

W. Haigis et al., "Comparison of immersion ultrasound biometry and partial coherence interferometry for intraocular lens calculation according to Haigis," *Graefe's Archive for Clinical and Experimental Ophthalmology*, vol. 238, No. 9, Sep. 1, 2000, pp. 765-773.

S. Norrby, "Using the lens haptic plane concept and thick-lens ray tracing to calculate intraocular lens power," *Journal Cataract and Refractive Surgery*, Surgery, Fairfax, VA, vol. 30, No. 5, May 1, 2004, pp. 1000, 1005.

(Continued)

*Primary Examiner* — Joseph P Martinez
*Assistant Examiner* — Brandi Thomas
(74) *Attorney, Agent, or Firm* — Patterson Thuente Pedersen, P.A.

(57) ABSTRACT

For the pre-operative calculation of the power of an intraocular lens, three input parameters are needed: the axial length of the eye (AL), the refractive power of the cornea, and the distance between the front of the cornea and the back focal plane of the intraocular lens, the so-called effective lens position (ELP). The invention shows a novel approach to the determination of the ELP.

3 Claims, 1 Drawing Sheet

(56) References Cited

OTHER PUBLICATIONS

T. Olsen, "Prediction of the effective postoperative (intraocular lens) anterior chamber depth," *Journal Cataract and Refractive Surgery*, Surgery, Fairfax, VA, vol. 32, No. 3, Mar. 1, 2006, pp. 419-424.

T. Olsen, "Improved accuracy of intraocular lens power calculation with the Zeiss IOLMaster," *ACTA Ophthalmologica Scandinavica* 2007, vol. 85, Feb. 2007, pp. 84-87.

J.A. Retzlaff et al., "Development of the SRK/T intraocular lens implant power calculation formula," *Journal Cataract and Refractive Surgery*, Surgery, Fairfax, VA, vol. 16, May 1990, pp. 333-339.

* cited by examiner

US 9,144,375 B2

METHOD FOR DETERMINING THE POWER OF AN INTRAOCULAR LENS

PRIORITY

This application is a continuation of PCT/EP2008/004406, filed Jun. 3, 2008. This application claims priority to U.S. Provisional Application, Ser. No. 60/933,012, filed Jun. 4, 2007, the disclosure of which is incorporated herein by reference.

TECHNICAL FIELD

Biometry, particularly measurement of geometrical parameters in the anterior segment, for the calculation of the refractive power of intraocular lenses (IOL).

BACKGROUND OF THE INVENTION

For the pre-operative calculation of the power of an intraocular lens, three input parameters are needed: the axial length of the eye (AL), the refractive power of the cornea, and the distance between the front of the cornea and the back focal plane of the intraocular lens, the so-called effective lens position (ELP).

To a good approximation, the post-operative axial length can be substituted by the corresponding value measured pre-operatively. The axial length can be measured either ultrasonically or optically using partial coherence interferometry (PCI). Also—at least for eyes that have not undergone keratorefractive surgery—the post-op corneal power can be predicted based on the pre-op measurement of the front surface corneal radii. This prediction is based on assumptions about the corneal index of refraction and the ratio of front and back surface corneal radii. Keratometry can be measured using manual or automatic optical keratometers, or extracted from a corneal topography obtained via Placido ring projection.

The effective lens position, on the other hand, is inherently a post-operative value. In fact the final position of an IOL does not manifest itself until a number of weeks after surgery, when the capsular bag has shrunk around the implant. A pre-op parameter the ELP approximately corresponds to is the distance from the front of the cornea to the front of the crystalline lens, the so-called anterior chamber depth (ACD). The ACD can be measured ultrasonically or optically using slit projection, or it can be predicted based on the diameter of the clear cornea (the so-called white-to-white distance, WTW) and its central curvature. In commonly used IOL calculation formulas, the ELP is predicted using an empirical fit of several parameters such as ACD and AL. Olsen has suggested that the prediction can be improved by inclusion of additional parameters such as the lens thickness (LT), corneal radius, and pre-op refraction (Acta Ophthalmol. Scand. 2007: 85: 84-87). Most commonly used IOL calculation formulas are based on the same vergence formula to model focusing by the intraocular lens; they only differ in the method for predicting ELP.

SUMMARY OF THE INVENTION

It is the purpose of this invention to provide a better ELP prediction by measuring a pre-op quantity that correlates closely to the post-op position of the IOL. In one preferred embodiment, an OCT device is used to indentify the iris root. The axial separation (ACD') between the front surface of the cornea and the plane of the iris root is then determined. The power of the intraocular lens is determined using the measured axial separation together with other measured parameters and empirically determined lens constants.

DETAILED DESCRIPTION OF THE PREFERRED EMBODIMENTS

Figure 1:
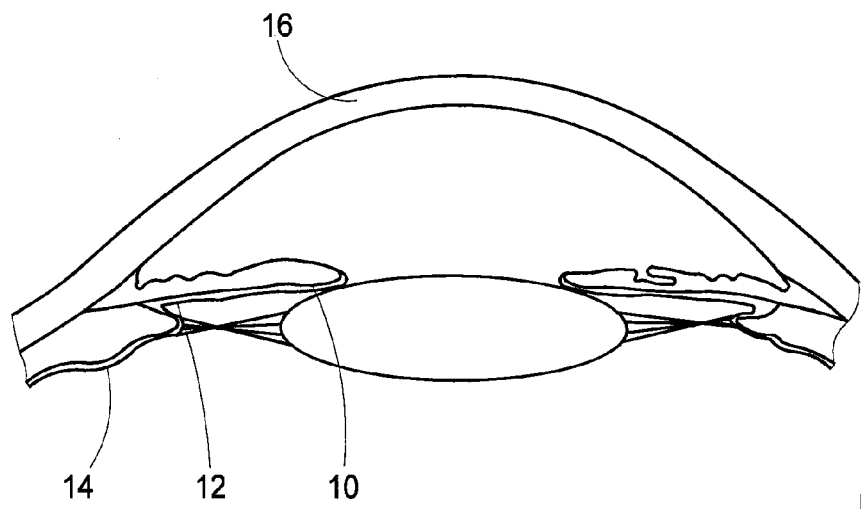
FIG. 1 is a cross sectional view of the eye.

As seen in the attached FIG. 1, in cross-sectional images of the anterior segment of the eye obtained by optical coherence tomography (OCT) at infrared wavelengths (e.g., 1310 nm) a strongly scattering layer 10 is visible near the back surface of the iris. This structure is commonly interpreted as the iris pigment epithelium. On the other hand, it has also been suggested that this scattering region may correspond to the iris dilator muscle.

At the periphery, the absorbing layer ends at a well-defined radial position (location 12 in FIG. 1), which is anatomically close to, or co-located with the iris root. In a meridional cross sectional OCT scan of the cornea the two peripheral end points of the scattering layer in the iris can be used to uniquely identify two iris root points. A line connecting the two iris root points can be used to define a root-to-root line. This line is shown as item 20 in FIG. 2.

Figure 2:
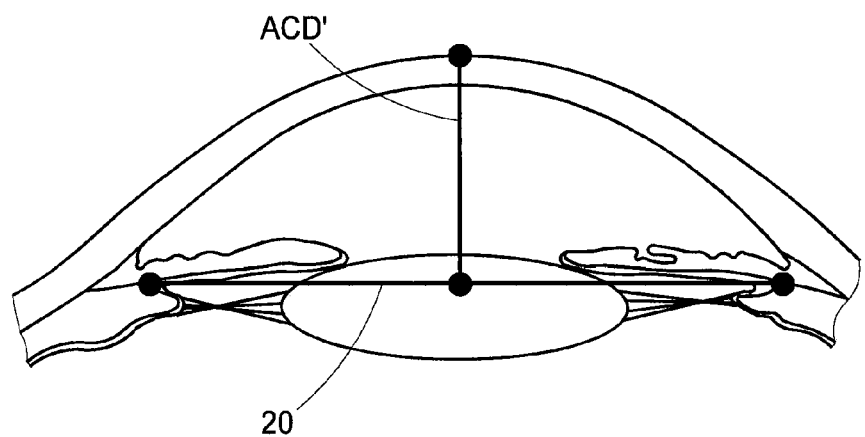
FIG. 2 is a cross sectional view of the eye illustrating the axial distance (ACD') between the front surface of the cornea and the plane of the iris root.

The separation of the root-to-root line from the front of the cornea 16 can be used to define a modified anterior chamber depth parameter ACD' (see FIG. 2). This can be defined in one of several different ways. Most simply, ACD' can be defined as the longest perpendicular distance from the root-to-root line to the front surface of the cornea. If the patient fixates in a direction parallel to the direction of the OCT scan during measurement, the line of sight can be uniquely identified in the acquired cross sectional image. ACD' can then alternatively be defined as the longest distance from the root-to-root line to the corneal front surface, measured parallel to the line of sight. Finally, the inner limits of the iris in the OCT scan can be used to mark the mid-point of the pupil along the root-to-root line. As a third alternative, the parameter ACD' can be measured from this mid-point to the corneal front surface, in a direction parallel to the line of sight.

The parameter ACD' can be used to predict the post-op effective lens position. Like with presently used formulas this can be done by empirically determining regression coefficients for a set of parameters, such as ACD', AL, and/or LT. Other measured parameters can include the two central radii of the corneal front surface. The prediction of ELP thus obtained can be used in IOL calculation formulas together with empirical lens constants.

Another possible approach relies on a measurement associated with a region located at the most anterior portion of a highly scattering layer posterior to the sclera (location 14 of FIG. 1). This layer is presumably a pigmented layer along the posterior boundary of the ciliary muscle. Similar to the approach shown in FIG. 2, a line connecting these two opposing points (14) can be drawn and the separation between this line and the front of the cornea (ACD"—not shown) can be defined and used to predict the IOL position after surgery. The value for ACD" can be used alone or in conjunction with the value for ACD'.

As is well known in the art, the determination of regression coefficients requires large data sets and produce formulas that have limited physical interpretation. The larger number of measurements to be included and the more complex the formula, the more data is required to develop those formulas. This can especially be a drawback in the modification of IOL calculation formulas for newly developed IOL's. The IOL calculation formula may instead take the form of regression formulas to calculate intermediate parameters such as the position of the IOL equator and the effective power of the lens. For example, the ELP is determined by a combination of anatomical features, such as the distance from the corneal vertex to the sulcus, by the design of the IOL and by surgical technique. Various surrogate measurements may be combined. For example the ACD' characterizes the position of the iris root. A combination of the traditional ACD, LT, anterior radius of curvature of the crystalline lens, and possibly also posterior radius of curvature of the crystalline lens, characterize the crystalline lens equator. These and other surrogate measurements (including ACD") can be combined into a regression formula for predicting the position of the IOL equator. The ELP prediction can then be calculated as a combination of the optical power, derived from the radii of curvature and index of refraction, the predicted IOL equator. The resulting ELP estimate can be integrated into an IOL calculation formula.

A particular embodiment of the inventive method consists in the following sequence: The axial length (AL) of a patient eye is measured using partial coherence interferometry (PCI), the modified anterior chamber depth ACD' is determined using optical coherence tomography (OCT) and the corneal power is determined using a suitable keratometric setup. The keratometric setup can be a stand-alone keratometer or integrated into a combination device such as the IOLMaster. After obtaining these measurements, the values are processed together with the desired target refraction using the Haigis-Formula to determine the required power of an intraocular lens.

In the Haigis-Formula
$$DL = \frac{n}{L-d} - \frac{n}{n/z - d}$$
with
$$z = DC + \frac{ref}{1 - ref\ dBC} \text{ and } DC = \frac{nC - 1}{RC}$$

where
DL: IOL-refraction
DC: cornea refraction
RC: cornea tradius
nC: refractive index of the cornea
ref: refraction to be obtained after surgery
dBC: spectacle distance from cornea
d: optical anterior chamber depth ACD
L: Eye length
n: refractive index of the eye (1.336)
d is normally predicted using a function based on a multivariable regression analysis from a large sample of surgeon and IOL-specific outcomes for a wide range of axial lengths (AL) and anterior chamber depths (ACD).

In the preferred embodiment, the modified anterior chamber depths parameter ACD' (or ACD") would be used in place of ACD in the regression fit.

In other common IOL formulas an expression equivalent to d is used too as the table shows:
SRK/T d=A-constant
Hoffer Q d=pACD
Holladay 1 d=Surgeon Factor
Holladay 2 d=ACD Also in these formulas d may be substituted by the modified anterior chamber depth ACD' (or ACD").

The invention is not limited to the embodiments described, also other uses of the measured values ACD' or ACD" for IOL calculation fall within the scope of protection.

The invention claimed is:

1. A method of determining the power of an intraocular lens implant comprising:
    measuring at least one of a crystalline lens radius of curvature or crystalline lens radii of curvature with one of an optical coherence tomography (OCT) system, a slit projection system and an Ultrasound system; and
    determining the power of the intraocular lens implant based on measurements made and additional measurements including one or more of the axial eye length, anterior cornea radius, posterior corneal radius, anterior chamber depth (ACD) and lens thickness.

2. The method as recited in claim 1, where said determining step is performed using a formula or a ray-tracing algorithm.

3. The method as recited in claim 1, wherein said determining step is further based on a calculation of effective lens position (ELP), wherein the ELP is derived from one or more additional parameters including the crystalline lens radius and the crystalline lens thickness.

* * * * *

UNITED STATES PATENT AND TRADEMARK OFFICE
CERTIFICATE OF CORRECTION

| | | |
|---|---|---|
| PATENT NO. | : 9,144,375 B2 | Page 1 of 1 |
| APPLICATION NO. | : 12/630656 | |
| DATED | : September 29, 2015 | |
| INVENTOR(S) | : Rudolf Murai Von Bünau et al. | |

It is certified that error appears in the above-identified patent and that said Letters Patent is hereby corrected as shown below:

On Title page of patent, Item (75) Inventors: delete "Burkhart" and insert --Burkhard--

Signed and Sealed this
Twenty-second Day of March, 2016

Michelle K. Lee
*Director of the United States Patent and Trademark Office*